United States Patent
Gottfries et al.

(12)

(10) Patent No.: US 6,368,590 B1
(45) Date of Patent: Apr. 9, 2002

(54) PHARMACEUTICAL PREPARATION AND METHOD FOR TREATMENT AND PREVENTION OF FIBROMYALGIA AND CHRONIC FATIGUE

(76) Inventors: Carl-Gerhard Gottfries, Svalebogatan 22, S-414 75 Göteborg (SE); Björn Regland, Störtfjallagatan 10, s-431 35 Mölndal (SE)

( * ) Notice: Subject to any disclaimer, the term of this patent is extended or adjusted under 35 U.S.C. 154(b) by 0 days.

(21) Appl. No.: 09/341,006
(22) PCT Filed: Dec. 23, 1997
(86) PCT No.: PCT/SE97/02208
§ 371 Date: Jun. 30, 1999
§ 102(e) Date: Jun. 30, 1999
(87) PCT Pub. No.: WO98/29133
PCT Pub. Date: Jul. 9, 1998

(30) Foreign Application Priority Data

Dec. 30, 1996 (SE) ................................................ 9604844

(51) Int. Cl.⁷ ................................................ A61K 35/74
(52) U.S. Cl. ...................................... 424/93.42; 514/52
(58) Field of Search .......................... 424/93.42; 514/52

(56) References Cited

U.S. PATENT DOCUMENTS 5,545,670 A * 8/1996 Bissbort et al.

FOREIGN PATENT DOCUMENTS

| WO | 9611014 | 4/1996 |
| WO | 9625155 | 8/1996 |

OTHER PUBLICATIONS

"Fibromyalgia Network" http://fmnetnew.com/pages/basics.html, May 2000.*

* cited by examiner

Primary Examiner—Francisco Prats
Assistant Examiner—Susan D. Coe
(74) Attorney, Agent, or Firm—Orum & Roth

(57) ABSTRACT

Use of a staphylococcus bacteria or a product thereof for the manufacture of a pharmaceutical preparation for treatment and/or prevention of fibromylagia and chronic fatigue syndrome. Preferably, the preparation also comprises vitamin $B_{12}$ and/or folacin. A method for treatment of and/or prevention of chronic fatigue syndrome or fibromylagia, characterized in that a staphylococcal preparation is administered in a therapeutically effective amount, preferably in combination with or parallel with vitamin $B_{12}$ and/or folacin. The preparation is preferably administered repeatedly, first 8–10 times during a period of 4–12 weeks when the dose is increased from a relatively lower dose the first administration to a relatively higher dose the last administration, then approximately once a week for 5–15 weeks, and finally approximately once a month for a period of 1–10 years.

1 Claim, No Drawings

PHARMACEUTICAL PREPARATION AND METHOD FOR TREATMENT AND PREVENTION OF FIBROMYALGIA AND CHRONIC FATIGUE

TECHNICAL FIELD OF THE INVENTION

The present invention relates to use of a staphylococcus vaccine for the manufacture of a pharmaceutical preparation. It also related to methods for treatment and/or prevention of fibromyalgia.

BACKGROUND OF THE INVENTION

Fibromyalgia and chronic fatigue are relatively new entities in the nosology of medical disorders. They encompass conditions with symptoms such as pain, fatigue and a wide range of other symptoms which seem to have many clinical and demographic characteristics (see e.g. Buchwald D., et al., Comparison of patients with chronic fatigue syndrome, fibromyalgia and multiple chemical sensitivities, Arch. Intern. Med. 154:2049–2053, 1994). Both diseases are diagnosed on the basis of clinical criteria.

Fibromyalgia

The term fibromyalgia was first delineated in 1981 by Yunus M. B., et al., in Primary fibromyalgia (fibrositis): A clinical study of 50 patients with matched normal controls, Semin. Arthritis Rheum., 11:151–171, 1981. However, the condition has been described in the literature of medicine since the middle of the 19th century (see e.g. Simons D. G., Muscle pain syndromes—part 1, Am. J. Phys. Med., 54:289–311, 1975). Fibromyalgia is often considered as a form of non articular rheumatism, which may be connected with the formulation in the classification set forth by the American College of Rheumatology (ACR 90) (see Wolfe F., et al., The American College of Rheumatology 1990 criteria for the classification of fibromyalgia; report of the multicentre criteria committee, Arthritis Rheum., 33:160–172, 1993). The most important criteria according to The American College of Rheumatology are widespread pain and the presence of at least 11 of 18 possible tender points, so called trigger points. In the consensus report from the 2nd World Congress of Myofascial Pain and Fibromyalgia in Copenhagen, Denmark, in 1992 the disease is described as follows: a painful, nonarticular condition predominantly involving muscles—the most usual cause for widespread musculoskeletal pain. The condition normally leads to persistent fatigue, non-refreshing sleep, as well as stiffness in the whole body. Fibromyalgia is a syndrome which encompasses headaches, irritable bowels, irritable bladder, dysmenorrhoea, cold sensitivity, Raynaud's phenomenon, restless legs, atypical patterns of numbness and tingling, intolerance to physical exertion, complaints of weakness etc. A varying percentage (20–25%) of patients suffering from fibromyalgia experience significant depression or anxiety.

It is common that the symptoms vary during the day and the year. The prevalence is high. Fibromyalgia is estimated to affect 2–6% of the population (see Wolfe F., et al. The prevalence and characteristics of fibromyalgia in the general population, Arthritis Rheum., 36((9S):57, 1993, and Buskila, D., et al., Assessment of nonarticular tenderness and prevalence of fibromyalgia in children, J. Rheumatol. 20:368–370, 1993). Fibromyalgia is more common in women than in men—less than 10% of the patients with fibromyalgia are men.

The aetiology of fibromyalgia is not known, but many factors are considered to have pathological importance. Though the pain is primarily located to the muscles, research findings do not support any explanation of the syndrome that is based on only peripheral changes. The type of pain—persistent pain even when the patient is resting—and the widely spread pain and soreness points at disorders in the central nociceptive system. The idea that there may be a central sensibilisation has been put forward by Bengtsson, A, et al., in Primary fibromyalgia. A clinical and laboratory study of 55 patients, Scand. J. Rheumatol. 15:340–347, 1986. Neuroendocrinological findings, such as disturbances in the metabolism of serotonine and insufficient release of growth hormone have been discussed as possible cause of some of the manifestations of fibromyalgia (see e.g. Bennett, R. M., et al., Low levels of somatomedin C in patients with fibromyalgia syndrome, Arthritis Rheum., 32:454–460, 1992, and Russel, I. J., Biochemical abnormalities in fibromyalgia syndrome, J. Musculoskeletal Fain, 2:101–115, 1994). Immunological factors have also been suggested as possible cause (see Klein, R., et al., Clinical relevance of antibodies against serotonin and gangliosides in patients with primary fibromyalgia syndrome, Psychoneuroendocrinology, 17:593:598, 1992).

No curative therapy for fibromyalgia is clinically available at present; only symptomatic treatment are offered to the fibromyalgic patients. Anaigetics, i.e. anti-inflammatory drugs and paracetamol, do not seem to redice the symptoms (see Lorenzen, I., Fibromyalgia—which is the best treatment? A personalized comprehensive, ambulatory, patient-involved management programme, Balliere's Clin. Rheum., 4:333–370, 1994). Treatment with antidepressant drugs has some effects (see Jacobsen, S., Chronic widespread muscoskeletal pain—the fibromyalgia syndrome, doctoral thesis, Copenhagen: Laegeforeningens forlag, 1994). Fibromyalgic patients can often improve their physical condition by physical training.

Chronic Fatigue Syndrome

This concept was introduced in 1988 by Centers for Disease Control (see Holmes G. P., et al., Chronic fatigue syndrome: a working case definition, Ann. Intern. Med., 108:387–389, 1988>. The syndrome was thoroughly defined and the diagnostic criteria was formulated. The obligate symptom was a fatigue of an incapacitating and chronic nature that should have lasted for at least six months. Eleven minor criteria were also defined and included: mild fever or chills, sore throat, painful lymph nodes, unexplained general muscle weakness, myalgia, prolonged general fatigue after exercise, headaches, migratory arthraigia, neurophysiologic complaints and sleep disturbances. There may also be physiological signs, such low fever, non-exudative pharyngitis, and palpable or tender cervical or axillary lymph nodes. In order to diagnose a patient with chronic fatigue syndrome, the patient must fulfill eight of the eleven criteria besides the chronic fatigue, or six of the eleven criteria and two of the physiological signs.

Many physicians were critical against these criteria an variations was used both in Australia and England. This led to a new definition, which was published in December 1994, (see Fukuda, K., et al., The chronic fatigue syndrome: a comprehensive approach to its definition and study, Ann. Intern. Med., 121:953–959, 1994). The new criteria are as follows: 1a) a clinical assessed, unexplained persistent chronic fatigue, that i) the patient has not experienced earlier, ii) is not the result of ongoing exercise, iii) does not improve with rest, iv) considerably reduces the potential for the patient to carry out previous activities at work or during leisure time; 1b) the patient should also have at least four of the following six symptoms, and they should have been manifested for at least six consecutive months, but not before the onset of the fatigue, i) a self-reported impairment of the short-term memory and the concentration ability, ii) a sore throat, iii) tender cervical or axillary lymph nodes, iv) muscular aches, v) headaches of a new type and severity, vi) fatigue upon awakening, vii) a feeling of being "ill" for more than 24 hours after physical exertions A possible connection between fatigue and infectious diseases, in particular viral diseases, has been proposed. Chronic fatigue syndrome is often considered to be the result of an acute infectious disease. Some infectious diseases that have been suggested as being of importance for chronic fatigue syndrome are infections caused by Epstein-Barr virus (EBV), human herpes virus type 6 (HBV-6), enterovirus and retrovirus, but no signs of a higher frequency of such diseases have been reported for patients suffering from chronic fatigue syndrome. There are reports on immunologic abnormalities, such as a decrease of subgroups of IgG, an increase of circulating antigen-antibody complexes, a lower activity of natural killer cells, a decrease of subgroups of the T-cells CD-4 and CD-8 and a decreased delayed hypersensitivity reaction on skin test antigens (see the review by Wilson, A., et al, Longitudinal study of outcome of chronic fatigue syndrome, Br. Med. J., 308:756–759, 1994). There are reports of a reduced amount of markers for cell mediated immunity compared to normal controls and patients with non melancholic depression. Studies in order to estimate the prevalence of chronic fatigue syndrome have been made at many research centres all over the world. A prevalence of 51–131 per 100,000 inhabitants has been reported for England, while preliminary statistic estimates from Centers for Disease Control indicate a prevalence of 2–7 per 100,000 inhabitants in four American states. An Australian study has reported a prevalence of 37 per 100,000 inhabitants.

The two syndromes, fibromyalgia and chronic fatigue syndrome, "overlap" and it has been suggested that it is in fact only one disease manifested in different ways.

SUMMARY OF THE INVENTION

The present invention relates to use of staphylococcus bacteria or a product thereof for the manufacture of a pharmaceutical preparation for treatment and/or prevention of fibromyalgia and chronic fatigue syndrome. It also relates to use of the manufactured pharmaceutical preparation.

Furthermore it relates to a method for treatment of and/or prevention of chronic fatigue syndrome or fibromyalgia, characterised in that a staphylococcal vaccine is administered in a therapeutically effective amount.

The characterising features or the invention will be evident from the following description and the appended claims.

DETAILED DESCRIPTION OF THE INVENTION

According to the present invention it is thus possible to manufacture a pharmaceutical preparation which can be used for treatment and prophylaxis of fibromyalgia and chronic fatigue syndrome. The main ingredient in the preparation is a substance functioning as a staphylococcal vaccine; it may be any kind of antigen products from Staphylococcus, or any kind of synthetically produced compound mimicking such a product.

The pharmaceutical preparation is preferably formulated for injection.

The preparation may advantageously further comprise vitamin $B_{12}$ and/or folacin. It has been found that a subgroup of patients suffering from fibromyalgia or chronic fatigue syndrome, also have levels of vitamin $B_{12}$ in their cerebrospinal fluid that are lower than normal, and levels of homocysteine that are higher than normal. The high levels of homocysteine is indication a lack of vitamin $B_{12}$ and folacin. It has been shown that this sub-groups of patients have a specific set of genes.

The preparation according to the intention may also comprise, such as pharmaceutically acceptable additives, e.g. solvents, adjuvants, carriers and/or preservatives.

The invention also relates to a method for treatment of and/or prevention of chronic fatigue syndrome or fibromyalgia, characterised in that a staphylococcal preparation is administered in a therapeutically effective amount.

The treatment is preferably conducted as a series of administrations with increasing doses during a specific period. Preferably the vaccine is administered in 8–10 increasing doses during 4–12 weeks, preferably 8–10 weeks. The reason for the increasing doses is that during the first week or weeks the patient will probably suffer from side effects, and it is therefore advantageously to start with a low dose. The side effects will diminish after some time.

In order to obtain the desired effect for a prolonged period of time the staphylococcal preparation should be administered at several occasions. It is not enough to administer the preparation just a few times since the patient then will not be cured at all, or the disease will reoccur within short. The first series of administrations is therefore followed by repeated administrations given approximately once a week for 5–15 weeks, preferably for 10 weeks.

To prevent recurrence the repeated administrations are then followed by a maintenance treatment with administrations approximately once a month, which preferably area continued for several years, such as 1–10 years, preferably approximately 5 years.

The doses in the repeated administrations the maintenance treatment are preferably constant and relatively high, for example the dose used in the last administration in the first series.

These repeated administrations result in an unspecific activation of the immune system over a long period of time.

The administrations can be made in any way known in the art, but they are preferably made as injections.

Vitamin B12 and/or folacin is preferably administered simultaneously or parallelly with the staphylococcal preparation.

If the known staphylococcal vaccine Staphypan Berna from the Serum- & Vaccine Institute Bern, Switzerland is used, a typical treatment schedule may be as follows: 8–10 administrations are made during a period of 4–12 weeks, preferably 8–10 weeks, wherein the dose of the staphylococcal preparation is gradually increased from 0.1 ml to 1 ml of the pure vaccine The increase depends on the response from the patient. It may e.g. be 0.1, 0.2, 0.3, 0.4, 0.5, 0.6, 0.7, 0.8, 0.9 and 1.0 ml, respectively. If the patient shows a strong local reaction it is possible to repeated a dose, before increasing it. The dose of the staphylococcal preparation in the repeated administrations and in maintenance treatment is 1 ml.

The invention will now be further explained in the following example. This example is only intended to illustrate the invention and should in no way be considered to limit the scope of the invention.

EXAMPLE

After a pilot study comprising eight patients was made, a placebo-controlled study was performed, comprising a group of patients fulfilling both the criteria for fibromyalgia and the criteria for chronic fatigue syndrome. The aim of the study was to decide the effect of treatment with staphylococcal preparation has on the symtomatology of fibromyalgia and chronic fatigue syndrome.

Patients 28 outpatients, all women between the ages of 33 and 64 (mean: 47.0±7.3) participated in the study. During the period the study lasted 4 patients were excluded; 1 due to cancer, 2 due to severe depression and 1 due to a psychotic disease. The patients were referred from health centres, other hospitals and psychiatric clinics in the area. They all met the criteria for fibromyalgia established by the American College of Rheumatology as well as the criteria for chronic fatigue syndrome outlined by the Center for Disease Control. All patients had a medical history of recurrent infections and/or a state of health indicating mild ongoing infections, such as mild fever or chills, a sore throat or tender lymph nodes (all these symptoms are included in the criteria for fibromyalgia and chronic fatigue syndrome, but they are not obligate).

All patient were chronically ill.

In average, the patients had suffered from fibromyalgia/chronic fatigue syndrome for 12.9 years (range 5–37 years).

Procedure

The 24 patients were randomly divided into the two groups. The study was double blind, i.e. nobody except for the nurse administering the injections knew what treatment was used. The nurse was not from the research group.

One group of patients was treated with a staphylococcus preparation (Staphypan Berna from the Serum- & Vaccine Institute Bern, Switzerland) and another group that received treatment with sterile water (placebo group). 13 patients received the treatment with the staphylococcal preparation and 11 patients were given the placebo. Active preparation was used in the concentrations 1%, 5%, 10%, 20%, 50% and 100% (i.e. 0.01, 0.05, 0.1, 0.2, 0.5 and 1.0 ml of fully potent preparation). All injections were made subcutaneously in the gluteal region once a week: the volume of both the staphylococcal preparation and the placebo injections was 1 ml. The staphylococcal preparation was given in concentrations increases every second week, 1% week 1 and 2, 5% week 3 and 4, 10% week 5 and 6, 20% week 7 and 8, 50% week 9 and 10 and undiluted preparation week 11 and 12. The injections with water were given at the same intervals, 1 ml each time.

After the controlled study was completed, those patients who had received placebo were offered active treatment. A long-term open study treatment was started. All the patients, including those from the pilot study, in all 32 patients, were offered prolonged active treatment with monthly doses. Those who accepted were assessed using the Comprehensive Psychopathological Rating Scale (CPRS) at three, six and 12 months during the first year and then once a year. The intervals between the doses varied from every other week up to every third month. The patients' work situation (working part- or full-time, being sick-listed, or receiving sickness pension) was assessed prior to and at the follow-up after completion of the controlled study.

23 of the 32 patients continued in the open study 20 of them have been treated between two and three years, and 3 patients have been treated between five and six years.

Laboratory Investigations

After inclusion in the study, all the patients underwent a clinical examination and a series of laboratory investigations.

Samples of blood of all patients and of cerebrospinal fluid of 12 patients were taken before the treatment trial began.

All the patients had normal laboratory test results regarding erythrocyte sedimentation rate, haematology count, liver enzymes, creatinine kinase and thyroid function tests. A dexamethasone suppression test was performed on 18 patients, which all had normal stress function. Antibodies against *Borrelia Burgdorferi* were investigated in plasma from 24 patients and in cerebrospinal fluid from 12 patients; the concentrations were normal. The concentrations of homocysteine, methylmalonic acid and vitamin $B_{12}$ were analysed both in plasma (24 patients) and in cerebrospinal fluid (12 patients). All patients had normal plasma levels of vitamin $B_{12}$ and methylmalonic acid, and all but two had normal plasma levels of homocysteine 10 out of 12 patients had levels of vitamin $B_{12}$ in cerebrospinal fluid lower than normal, 11 of 11 had high levels of homocysteine in the cerebrospinal fluid and 2 had levels of methylmalonic acid in the cerebrospinal fluid higher than normal.

Psychometric Assessments

Zung's self-rating depression scale (Zung, W. W. K., A self rating depression scale, Arch. Gen. Psychiatry, 12:63–70, 1965) consists of 20 items measuring both somatic and affective components of depression.

The Comprehensive Psychopathological Rating Scale, CPRS, (Asberg, M., et al., A comprehensive psychopathological rating scale, Acta Psychiatr. Scand, 1978(Suppl. 271):5–27) includes 65 reported and observed items. The items cover psychiatric symptoms of both neurotic and psychotic dimensions. There are seven scale steps for each item, with 0 indicating normality and 6 maximum severity of a symptom. In the present study, 15 reported items measuring symptoms of interest in neurasthenia were selected (CPRS-15) (Knave, B, et al., Neurasthenic symptoms in workers occupationally exposed to jet fuel, Acta Psychiatr Scand. 60:39–49, 1979). One of the selected items measured fatiguability (CPRS-F) and another measured aches and pain (CPRS-P). The other CPRS items measured sadness, anxiety, aggressiveness, depressed mood, suicidal thoughts, hypochondria, being worried, phobias, concentration difficulties, memory difficulties, sleep difficulties, vegetative symptoms, and symptoms of muscle tension CPRS-15 assessments were made before and during treatment at 4, 8, and 12 weeks. CPRS-15 was also used in the open follow-up study.

Clinical Global Impressions, CGI, (National Institute of Mental Health, 1970) is an observation rating scale. On this scale, the severity of illness can be rated from 1 to 7, with 1 indicating "normal, not ill at all", and 7 "among the most extremely ill patients". Global improvement can also be rated from 1 to 7 on the CGI, with 1 indicating very great improvement, 4 no change, and 7 very great impairment. In the present study, "severity of illness" was rated before treatment as a measure of the condition of the patients. Improvement was rated after 12 weeks of treatment.

Pain Assessment

The patients' pain levels were measured before treatment, every second week during treatment, and one month after treatment using the Visual Analogue Scale, VAS. The VAS was a 100 mm long, horizontally oriented line whose endpoints were designated "no pain" and "the worst pain imaginable". The patients were told to indicate their "perceived momentary pain" and also "average pain intensity" during the last week.

Pressure Pain Threshold Measurements

Pressure pain thresholds (PPT) were determined with a hand-held electronic pressure algometer (Somedic*, Sweden). The stimulation probe has a circular tip (10 mm in diameter) and is connected to a pressure transducer built into a gun-shaped handle. The signal from the pressure transducer is amplified in a main unit, and the pressure is shown in kPa on a digital display. A display consisting of horizontal light bars indicates whether the applied pressure is above or below a pre-set rate. In the present study the pre-set rate was 30 kPa/s. When the PPT is reached, the subject activates a hand-held push-button, which freezes the digital display. The PPT was defined as the minimal pressure (kPa/cm$^2$) that induces pairs. The patients were instructed to activate the push-button when the sensation changed from one of pressure alone to one of mixed pressure and pain. The algometer was calibrated before each patient was tested.

PPT was determined at six paired (left, right) locations of trigger points chosen in accordance with the trigger sites in fibromyalgia patients given by the American College of Rheumatology. The trigger points included the trapezium at the midpoint of its upper border, the second rib at the costochondral junction, the lower arm 20 mm distal to the lateral epicondyle of the humerus, and the gluteal region at the upper outer quadrant of the buttocks.

Control points were located on both thumb nails and on the forehead 25 mm above the midpoint of the eyebrows (bilaterally). The structures were localised by palpation and were marked with a pen.

Each trigger point and control point was tested three times, three minutes apart, in each session. The median values of the three assessments at each location were added to yield a total tenderness score. This total tenderness score was divided by the number of local points measured to establish an average of the trigger point and the control point, respectively. The thresholds were measured before start of treatment, after twelve weeks' treatment and at a follow-up four weeks after cessation of treatment.

Statistics

Values are expressed as means, with standard deviations (SD) in parentheses, if not otherwise stated. The statistical analyses were conducted using Wilcoxon's Signed Rank Test for paired samples and Mann-Whitney's U test for calculating group differences. All tests were two-tailed. Statistical significance was considered when $p<0.05$. Correlations were tested with Spearman's Rank Correlations.

Results

In the laboratory test, there were no significant differences between the two groups prior to treatment.

10 of 12 patients had subnormal levels of $B_{12}$ in the cerebrospinal fluid. Significant correlations between the levels of $B_{12}$ in the cerebrospinal fluid and the CPRS items "fatiguability" and "memory difficulties", and the total CPRS scores were found. The scores for "muscle tension", "hypochondria" and "pain" was bordering on being significantly related the levels of $B_{12}$ in the cerebrospinal fluid. The correlation was that the lower the levels of $B_{12}$, the higher the scores on evaluated symptoms. This is shown in table 1.

All patients had pathologically high levels of homocysteine in the cerebrospinal fluid. There was also significant correlations between the levels of homocysteine in the cerebrospinal fluid and the CPRS items "fatiguability" and "pain"; the higher the level of homocysteine, the more pronounced the fatigue and the pain. This is also shown in table 1.

Clinical Global Impression

All the patients were assessed using the CGI to determine their severity of illness prior to taking part in the study. 18 of the 24 patients were assessed as being moderately ill, 5 as being markedly ill, and 1 as being severely ill. There were no significant differences between the two groups prior to treatment.

The patients were assessed with regard to their global improvement after 12 weeks' treatment. Each patient's condition was compared to her condition at admission to the study. 7 of the 13 patients who received the staphylococcal preparation were assessed as being minimally improved, 3 as being much improved, and the remaining 3 were unchanged. In the placebo group 3 patients were minimally improved, while the remaining 8 were unchanged. The improvement in the group with active treatment was statistically significant ($p<0.05$) compared to the improvement in the placebo group.

Comprehensive Psychopathological Rating Sale (CPRS)

The mean of the total CPRS scores (CPRS-15) in the group with active treatment (n=13) was 715.4 (3.9) before treatment and 10.5 (5.1) after treatment (week 12). This decrease was significant ($p<0.01$). The placebo group (n=11) had a mean of 15.0 (4.5) before treatment and 12.8 (5.6) after treatment, which did not show any significant improvement. This is shown in table 2.

The fatigue item (CPRS-F) decreased from 2.2 (0.4) to 1.5 (0.5) ($p<0.01$) in the group with active treatment. In the placebo group, the same item showed a non-significant decrease from 2.3 (0.5) to 2.1 (0.2) (p=0.19).

The patients pain reports (CPRS-P) yielded similar results. The mean score in the group with active treatment decreased from 2.3 (0.4) to 1.9 (0.6), ($p<0.01$). In the placebo group, there was no change in CPRS-P [2.2 (0.6) compared to 2.2 (0.3) (p=0.94)].

Intergroup differences regarding CPRS-F and CPRS-P week 0 and week 12 were analysed. For the actively treated patients, the mean score on CPRS-F reduced significantly more than for the patients in the placebo group ($p<0.05$). The difference borders on significance regarding CPRS-P. This is shown in table 2.

Depressive Symptoms

Zung's self-assessment depression scale showed a significant decrease in the placebo group. The decrease in the group with active treatment did not reach a significant level. The placebo group value decreased from 47.2 (5.9) to 41.6 (9.1) ($p<0.05$), and the group with active treatment value decreased from 43.8 (9.4) to 39.1 (7.5) (P=0.12). This is also shown in table 2.

Pain Severity

Before treatment there were no significant differences between the two groups regarding the two pain severity criteria measured with the visual analogue scale (VAS).

Momentarily Perceived Pain:

Before the treatment started, the group with active treatment had a mean value of 5.3 (2.2). A significant change was seen after 12 weeks' treatment, as the mean value decreased to 3.8 (2.0) ($p<0.05$). Four weeks post treatment, the mean VAS value was 4.1 (2.6) (n=10). The placebo group reported a mean pre-treatment mean value of 6.0 (1.2). After treatment the mean was reduced to 4.4 (1.3) ($p<0.05$). Four weeks post treatment, the mean VAS value was 4.1 (17).

Average—Last Week:

Before treatment, the group with active treatment had a mean value of 5.7 (2.1). The post-treatment mean value was 4.0 (2.0) ($p<0.05$). After four weeks' withdrawal, the mean value was 4.2 (2.7). The placebo group did not show significant decrease (6.0 (3.9), 4.9 (1.6). Four weeks post treatment, the mean had increased to 5.6 (2.9).

The correlation was high between the "momentarily perceived pain" and "average pain last week" both before (0.93) and after (0.93) treatment, and at follow-up (0.88), see table 2.

Pressure Pain Thresholds

There were no significant differences between the groups in PPT before treatment. In the group with active treatment the mean value of the TP was 48 (21) kPa, while the placebo group had a mean value of 95 (28) kPa. The CP values were 158 (109) kPa in the group with active treatment and 103 (57) kPa in the placebo group.

When the treatment-was completed 12 weeks later, both groups had increased their PPT in TP. In the group with active treatment it had increased to 124 (33) kPa (p<0.05) and in the placebo group to 115 (32) kPa (n.s.).

The PPT in CP also increased, but the increases were not significantly. The value in the vaccinated group was 211 (98) kPa and in the placebo group it was 132 (45) kPa (n.s.), see table 2.

Follow-up Study

Following the controlled study, 32 patients, including those in the present and the pilot study, were offered treatment with the staphylococcus preparation in a long-term open study. 24 patients chose to continue with the treatment. 3 of the 8 patients from the pilot study have been in treatment between three and four years. Of 15 the 24 patients in the controlled study, 20 have been treated between one and two years. 19 of these 20 patients were on the sick-list or received sickness pension prior to the start of treatment, and 1 patient was employed part-time. At the one-year follow-up after the completed study, 9 of the 20 patients were in full- or part-time paid employment, while 1 patient was taking part in a work experience program, and 1 was at the middle of a two-year training to become a nurse.

The mean total CPRS-15 score for these 23 (total number of patients still receiving active treatment) patients prior to treatment was 15.1 (3.2). At the one-year follow-up, the mean CPRS score was 9.1 (4.2). After four years, the mean CPRS-15 score for the 3 patients from the pilot study still receiving treatment was 6.8 (0.8).

The treatment strategy used in the above study, which is preferable but which does not limit the scope of the invention, is a series of administrations staphylococcal preparation given approximately once a week during a period of some months, for example three months and thereafter long-term treatment with monthly administrations.

In the example the preparation used is the staphylococcal vaccine Staphypan Berna, but it is of course possible to use other staphylococcal preparations.

TABLE 1

Spearman's rank correlation coefficients for correlations between rated CPRS items and vitamin $B_{12}$ (CSF-B12) and homocysteine (CSF-HCY) levels in the cerebrospinal fluid

|  | CSF-B12 (n = 12) | CSF-HCY (n = 11) |
| --- | --- | --- |
| Sadness | −0.30 | −0.17 |
| Inner tension | −0.52[+] | 0.00 |
| Hostile feelings | −0.44 | 0.13 |
| Pessimistic thoughts | −0.03 | 0.09 |
| Suicidal thoughts | 0.08 | −0.14 |
| Hypocondriasis | −0.52[+] | 0.00 |
| Worrying over trifles | −0.41 | 0.32 |
| Phobias | −0.59 | 0.71* |
| Famiguability | −0.66* | 0.63* |
| Concentration difficulties | −0.16 | −0.17 |
| Failing memory | −0.73** | 0.51 |
| Reduced sleep | −0.33 | 0.29 |
| Autonomic disturbances | −0.25 | 0.11 |
| Aches and pains | −0.51[+] | 0.13 |
| Muscular tension | 0.41 | −0.51 |
| CPRS-15 | −0.80** | 0.28 |

TABLE 1-continued

Spearman's rank correlation coefficients for correlations between rated CPRS items and vitamin $B_{12}$ (CSF-B12) and homocysteine (CSF-HCY) levels in the cerebrospinal fluid

|  | CSF-B12 (n = 12) | CSF-HCY (n = 11) |
| --- | --- | --- |
| CPRS-D6 | −0.44 | 0.12 |
| CPRS-N3 | −0.67[+] | 0.49 |

[+]p < 0.10
*p < 0.05
**p < 0.01

TABLE 2

Results of various measurements in two patient groups, one receiving active treatment with the staphylococcal preparation (n = 13), the other receiving placebo (sterile water, n = 11)

| Variables and score range | Time | Group with active treatment Mean (SD) n = 13 | Placebo group Mean (SD) n = 11 |
| --- | --- | --- | --- |
| CPRS-fatiguability (0–6) | week 0 | 2.2(0.4) } ** | 2.3(0.5)[a] |
|  | week 12 | 1.5(0.5) | 2.1(0.2) |
|  | 4 weeks post treatment | 2.3(0.3) }* | 2.4(0.2) |
| CPRS-pain (0–6) | week 0 | 2.3(0.4) } ** | 2.2(0.6)[a] |
|  | week 12 | 1.9(0.6) | 2.2(0.3) |
|  | 4 weeks post treatment | 2.4(0.6) }# | 2.2(0.3) |
| CPRS-15 (0–90) | week 0 | 15.4(3.9) } ** | 15.0(4.5) |
|  | week 12 | 10.5(5.1) | 12.8(5.6) |
|  | 4 weeks post treatment | 15.6(6.6) }# |  |
| ZUNG (25–100) | week 0 | 43.8(9.4) | 47.2(5.9) }* |
|  | week 12 | 39.1(7.5) | 41.6(3.9) |
| VAS pain (0–10) (tris moment) | week 0 | 5.3(2.1) }* | 6.0(1.2) }* |
|  | week 12 | 3.8(2.0) | 4.4(1.3) |
|  | 4 weeks post treatment | 4.1(2.6) (n = 10) | 4.1(1.7) (n = 9) |
| VAS pain (0–10) (last week) | week 0 | 5.7(2.1) } | 6.0(3.9) |
|  | week 12 | 4.0(2.0) | 4.6(1.6) |
|  | 4 weeks post treatment | 4.2(2.7) (n = 11) | 5.6(2.9) (n = 9) |
| Pain threshold (kpa) tender points | week 0 | 48(21) }a | 95 (28) |
|  | week 12 | 124(33) | 115 (32) |
| Control points | week 0 | 158(109) }ns | 103(57) |
|  | week 12 | 211(98) | 132(45) | p < 0.10
*p < 0.05
**p < 0.01
[a]intergroup differences (Mann-Whitney U-test): CPRS-fatiguability p < 0.05, CPRS-pain p < 0.10

What is claimed is:

1. A method for treatment of fibromyalgia and chronic fatigue syndrome comprising the steps of:
   a) administering a staphylococcal preparation, weekly, in increasing amounts from 0.1 ml to 1.0 ml over a period of 8–10 weeks; and then
   b) monthly in a 1 ml dosage for 8–10 years.

* * * * *